United States Patent
Huh et al.

(10) Patent No.: US 10,329,527 B2
(45) Date of Patent: Jun. 25, 2019

(54) SPHEROID FORMING CULTURE CONTAINER USING TEMPERATURE-SENSITIVE GLYCOL CHITOSAN DERIVATIVE, AND SPHEROID FORMING METHOD USING SAME

(71) Applicants: THE INDUSTRY & ACADEMIC COOPERATION IN CHUNGNAM NATIONAL UNIVERSITY (IAC), Daejeon (KR); KOREA RESEARCH INSTITUTE OF CHEMICAL TECHNOLOGY, Daejeon (KR)

(72) Inventors: Kang Moo Huh, Daejeon (KR); Sun Woong Kang, Daejeon (KR); Han Chang Kang, Bucheon (KR); Hye Eun Shim, Busan (KR); Ik Sung Cho, Daejeon (KR); Myeong Ok Cho, Daejeon (KR)

(73) Assignees: THE INDUSTRY & ACADEMIC COOPERTAION IN CHUNGNAM NATIONAL UNIVERSITY (IAC), Daejeon (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/504,062

(22) PCT Filed: Jul. 30, 2015

(86) PCT No.: PCT/KR2015/007993
§ 371 (c)(1),
(2) Date: Feb. 15, 2017

(87) PCT Pub. No.: WO2016/036011
PCT Pub. Date: Mar. 10, 2016

(65) Prior Publication Data
US 2017/0275586 A1    Sep. 28, 2017

(30) Foreign Application Priority Data

Sep. 2, 2014 (KR) ........................ 10-2014-0116020

(51) Int. Cl.
| C12N 5/00 | (2006.01) |
| C12M 1/22 | (2006.01) |
| C12M 1/00 | (2006.01) |

(52) U.S. Cl.
CPC .......... *C12N 5/0068* (2013.01); *C12M 23/10* (2013.01); *C12M 23/20* (2013.01); *C12N 2533/72* (2013.01)

(58) Field of Classification Search
None
See application file for complete search history.

(56) References Cited

U.S. PATENT DOCUMENTS

| 2004/0197907 | A1 | 10/2004 | Kataoka |
| 2009/0246872 | A1 | 10/2009 | Ozawa |
| 2010/0222538 | A1 | 9/2010 | Kwon |
| 2015/0291705 | A1 | 10/2015 | Huh et al. |

FOREIGN PATENT DOCUMENTS

| KR | 10-0675533 | 1/2007 |
| KR | 10-2008-0095182 | 10/2008 |
| KR | 10-2012-0097865 | 9/2012 |
| KR | 10-1341572 | 12/2013 |
| KR | 10-1362293 | 2/2014 |
| KR | 10-2014-0055257 | 5/2014 |

OTHER PUBLICATIONS

Gao, Wen Juan et al., "Functional enhancement of chitosan and nanoparticles in cell culture, tissue engineering, and pharmaceutical applications", Frontiers in Physiology, Aug. 21, 2012, vol. 3, Article No. 321 (Internal pp. 1-13).
Junji Fukuda et al., "Micromolding of photocrosslinkable chitosan hydrogel for spheroid microarray and co-cultures", Biomaterials, Oct. 1, 2006, vol. 27, pp. 5259-,5267.
Li, Zhiqiang et al., "Effect of cell culture using chitosan membranes on stemness marker genes in mesenchymal stem cells", Molecular Medicine Reports. Apr. 10, 2013, vol. 7, pp. 1945-1949.
Cameron L. Nemeth et al., "Enhanced Chondrogenic Differentiation of Dental Pulp Stem Cells Using Nanopatterned PEG-GelMA-HA Hydrogels", Jun. 30, 2014, vol. 20, Nos. 21-22, pp. 2817-2829
Cho, Myeong Ok et al., "Facile spheroid forming method using thermo-sensitive hydrogel based on glycol chitosan", Proceedings of the Polymer Society of Korea Fall Meeting, Apr. 8, 2015, p. 1442, vol. 40, No. 1, Document No. 3Ps-282.

*Primary Examiner* — Jennifer M. H. Tichy
(74) *Attorney, Agent, or Firm* — Lex IP Meister, PLLC (57) ABSTRACT

Disclosed is a spheroid forming culture container using a temperature-sensitive glycol chitosan derivative and a spheroid forming method using the same. In the disclosed spheroid forming culture container, a surface of a culturing space is coated with a glycol chitosan derivative having reversible sol-gel transition characteristic depending on temperature.

7 Claims, 10 Drawing Sheets

SPHEROID FORMING CULTURE CONTAINER USING TEMPERATURE-SENSITIVE GLYCOL CHITOSAN DERIVATIVE, AND SPHEROID FORMING METHOD USING SAME

TECHNICAL FIELD

The present invention relates to a spheroid forming culture container, which is a 3-dimensional cell group and equivalently functions as in vivo, and to a method for forming a spheroid using the same.

BACKGROUND ART

Cells and tissue in the body are proliferated, differentiated, and developed through interaction of very complex 3-dimensional structures. However, most of cell culturing is performed on an impermeable and flat 2-dimensional plane. Therefore, 2-dimensional cell culturing has a limitation in properly mimicking in vivo cellular environment.

Recently, culturing of a spheroid, which is a 3-dimensional cell group and equivalently functions as in vivo, receives attention. Since cell aggregation is induced to mimic a cancer and a method of grafting aggregated cells is used in transplantation of islet cells in order to induce normal secretion of insulin for treatment of diabetes, mass production of a spheroid is required. Further, in accordance with development of stem cell research, various methods are attempted to culture embryonic stem cells in 3-dimension and apply the resultant to the study about various differentiation mechanisms.

Examples of typical 3-dimensional cell culturing methods include a hanging-drop method, a rotary culture method, a centrifuge method, a micromolding method and so forth. For example, Japanese Laid-open Patent No. 6-327465 discloses a method of seeding a plurality of single cells in a well having a cone shape bottom and culturing a spheroid by aggregating and dividing the single cell on the bottom, and Korean Registered Patent No. 10-1341572 discloses a culturing method using a 3-dimensional cell culturing device including: a plate part; and a plurality of cell receiving parts which are extended from one end of the plate part and include a hollow-type tube.

It has been expected that these 3-dimensional cell culturing method is used in various fields of industry such as regeneration medicine, hybrid artificial organs, production of biobeneficial materials, research•investigation of tissue or organ of organisms, screening of new drugs, an alternative method of animal testing to evaluate influence of an endocrine disruptor, a cell chip having a function as a sensor and so forth.

However, these typical 3-dimensional cell culturing methods are problematic in that: a separate culturing tool is required; the culturing method is complicate; and also required time is long.

DISCLOSURE OF THE INVENTION

Technical Problem

An object of the present invention is to provide a spheroid forming culture container, and a spheroid forming method by using the container, wherein the container is capable of forming 3-dimensional cell group, i.e., spheroid in a short period of time with a simple method by using a glycol chitosan derivative having reversible sol-gel transition characteristic depending on temperature.

Technical Solution

Therefore, the present invention provides a spheroid forming culture container in which a surface of a culturing space is coated with a glycol chitosan derivative of the following Chemical Formula 1:

[Chemical Formula 1]

(wherein,
$R_1$ is a C1-C18 alkyl group;
x, y, and z are integers from 10 to 10000; and mol % thereof is $0.05 \leq x \leq 0.8$, $0.05 \leq y \leq 0.15$, and $0.05 \leq z \leq 0.9$).

The present invention also provides a spheroid forming method using a spheroid forming culture container in which a surface of a culturing space is coated with the glycol chitosan derivative of Chemical Formula 1 during cell culturing.

Advantageous Effects

According to the present invention, a cell spheroid is obtainable in a short period of time with a relatively simple method of culturing cells by using a culture container coated with a glycol chitosan derivative allowing of reversible sol-gel transition depending on temperature and having less cell hydrophilicity; and then separating the formed spheroid by simply changing the temperature. The resulting cell spheroid may maintain specific functions of cells for a long period of time.

BRIEF DESCRIPTION OF THE DRAWINGS

FIG. 3a) is an image showing sol-gel behavior of N-hexanyonylate glycol chitosan according to an embodiment of the present invention, and b) is a graph showing changes in sol-gel transition temperature according to the concentration of N-hexanyonylate glycol chitosan.

MODE FOR CARRYING OUT THE INVENTION

Hereinafter, the present invention will be described in more detail.

The present invention suggests a spheroid forming method, which is a 3-dimensional cell group, through cell culture using a glycol chitosan derivative having temperature sensitivity allowing reversible sol-gel transition at a certain temperature.

Specifically, the present invention employs a glycol chitosan derivative in which a part of amine groups at position 2 is substituted with an acetyl group and an alkylacyl group having $R_1$, which is a C1-C18 alkyl group, in a glycol chitosan derivative having a substituting glycol group at position 5 as shown in the following Chemical Formula 1:

[Chemical Formula 1]

(wherein, $R_1$ is a C1-C18 alkyl group;

x, y, and z are integers from 10 to 10000; and mol % thereof is $0.05 \leq x \leq 0.8$, $0.05 \leq y \leq 0.15$, and $0.05 \leq z \leq 0.9$).

As the glycol chitosan derivative, a material having a phase transition critical temperature of 37° C. or less is preferably used. More preferably, N-propionylate glycol chitosan, N-butyroylate glycol chitosan, N-pentanyonylate glycol chitosan, N-hexanyonylate glycol chitosan and N-acetylate glycol chitosan are used.

The glycol chitosan derivative of the present invention forms hydrogel without formation of chemical cross-linking at a temperature the same as or higher than the phase transition critical temperature, and performs phase transition from a gel state to a sol state at a temperature lower than the phase transition critical temperature.

The sol-gel transition occurs within in a certain degree of substitution. The critical substitution degree allowing of sol-gel transition is 20-95% (corresponding to Z value in Chemical Formula 1), and preferably 20-70%. Beyond the range, reversible sol-gel transition does not occur. The critical substitution degree may vary depending on types of the substitution group. The sol-gel transition for —NH acyl glycol chitosan prepared in an example of the present invention occurs within a substitution degree ranging from 20 to 67%.

The sol-gel critical temperature may vary depending on the molecular weight of a glycol chitosan derivative having a hydrophobic substitution group. Preferably, the derivative having a weight-average molecular weight of 100-5,000,000, and preferably 200-100,000 may be used.

The spheroid forming culture container of the present invention has an inside culturing space having a surface coated with a glycol chitosan derivative as described above.

Specifically, the surface of the culturing space refers to a part where the culture container contacts with cells.

The material and shape of the culture container are not specifically limited. As an example, the material may be any one of acrylic-based resin, polylactic acid, polyglycolic acid, styrene-based resin, acrylic styrene-based copolymer resin, polycarbonate-based resin, polyester-based resin, polyvinyl alcohol-based resin, ethylene vinyl alcohol-based copolymer resin, thermoplastic elastomer, vinyl chloride-based resin, and silicone resin or combination thereof.

Since the glycol chitosan derivative has low affinity with cells, the derivative does not bind to cells during cell culture and induces cell aggregation. Thus, a spheroid, which is a 3-dimensional cell group, may be effectively formed when cell culturing is performed in a culture container on which the glycol chitosan derivative is coated.

The glycol chitosan derivative is preferably included in a content of 4 wt % or more in a coating solution in order to achieve a phase transition critical temperature suitable for cell culturing. The coating solution includes the glycol chitosan derivative and a medium for culturing cells.

The spheroid forming method of the present invention employs the culture container during the cell culture.

In the present invention, the available cells for culturing do not specifically limited, and any type of cells known in the art may be used. As an example, epithelial cells, fibroblasts, osteoblasts, condrocytes, myocardial cell, hepatocytes, human-derived cord blood cells and mesenchymal stem cells, vesicular endothelial progenitor cells, embryonic stem cells, myoblasts, cardiac stem cells, and so forth may be used. The mesenchymal stem cells may be isolated from bone marrow, muscle, fat, cord blood, amnion, or amniotic fluid, but not limited thereto. The vesicular endothelial progenitor cells may be isolated from blood, cord blood, embryo, or bone marrow, but not limited thereto.

The glycol chitosan derivative of the present invention having a phase transition critical temperature of 37° C. or less, which is a normal temperature for cell culturing, forms hydrogel without formation of chemical cross-linking during cell culture to thereby effectively induce spheroid formation. Also, after formation of a spheroid having a certain size, due to phase transition from the gel state to the sol state again when the temperature is reduced to a temperature lower than the phase transition critical temperature for collection, the spheroid is easily isolated.

Hereinafter, preferred examples and experimental examples of the present invention are described. The examples and experimental examples below are provided so that the present invention is more clearly described, and the scope of the present invention is not limited to the examples below.

Preparation Example 1: N-Hexanyonylate Glycol Chitosan

As shown in the following Reaction Formula 1, 10 g of acetylated glycol chitosan (weight-average molecular weight of 400 kDa, acetylation degree of 9.34±2.50% (measured with $^1$H NMR, Sigma-Aldrich, Inc., USA) was dissolved in 1000 ml of distilled water in a rector. Then, hexanoic anhydride was added such that a molar ratio between glycol chitosan and hexanoic anhydride becomes 0.4, and thereafter the resultant was stirred for 48 hours at room temperature.

After the reaction has been completed, precipitation using cold acetone was performed to obtain the reactant, and solid was obtained through centrifugation. The separated solid was dialyzed with distilled water for 3 days by using a dialysis membrane having a molecular weight cut-off of 2 kDa, and then freeze-dried. The substitution degree (%) was 36.5±2.0, and yield was 82.3%.

[Reaction Formula 1]

$^1$H-NMR Analysis

Figure 1:
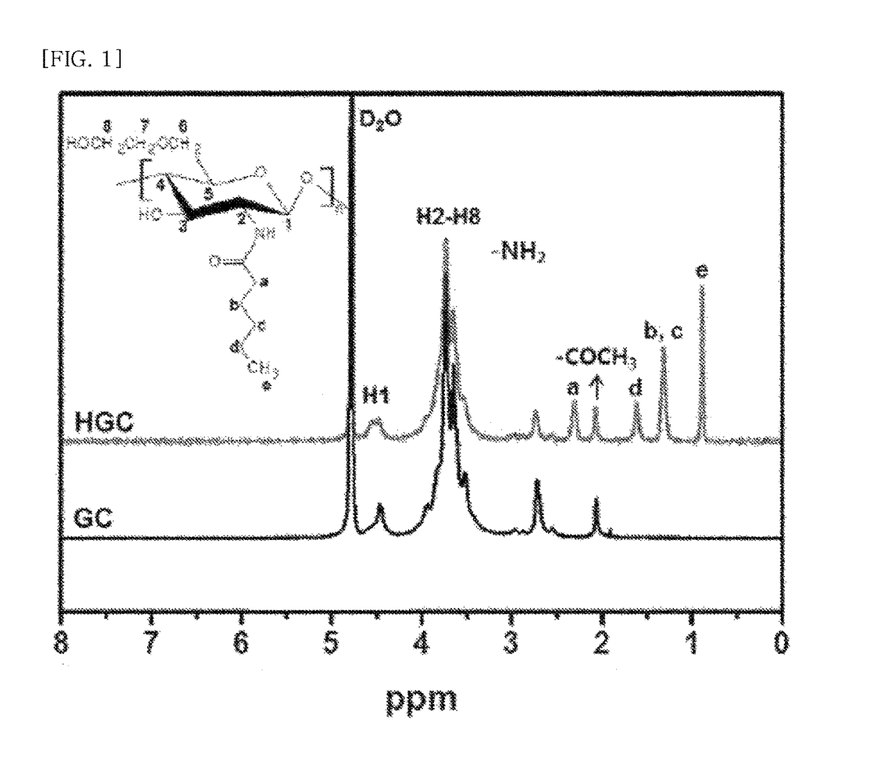
FIG. 1 is an $^1$H-NMR spectrum of N-hexanyonylate glycol chitosan according to an embodiment of the present invention.

To investigate whether —NH alkylacyl glycol chitosan prepared as above was synthesized or not, $^1$H-NMR analysis was performed. The result is shown in FIG. 1.

For an NMR sample, $D_2O$ was used as a solvent, and preparation was performed by dissolving a polymer to 1 wt %. For both GC and HGC spectra, it has been found that $D_2O$ peak, which was used as a solvent, was shown at $\delta$=4.71 ppm, and H2-H8 peak for glucopyranosyl ring was observed at $\delta$=3.68 ppm. In addition, —N$\underline{H}_2$ peak was observed at $\delta$=2.74 ppm, and —CO—C$\underline{H}_3$ (which is an acetyl group) peak was observed at $\delta$=2.02 ppm. For a spectrum of N-hexanyonylate glycol chitosan in which a hexanoyl group is added to glycol chitosan, —CO—C$\underline{H}_2$— at $\delta$=2.31 ppm, and —CO—CH$_2$—CH$_2$—CH$_2$—C$\underline{H}_2$—CH$_3$ peak at $\delta$=1.62 ppm were further observed, and a peak corresponding to —CO—CH$_2$—CH$_2$—C$\underline{H}_2$—CH$_2$—CH$_3$ appeared at $\delta$=1.32 ppm. Additionally, —CO—CH$_2$—CH$_2$—CH$_2$—CH$_2$—C$\underline{H}_3$ peak was found at $\delta$=0.89 ppm.

FT-IR Analysis

Figure 2:
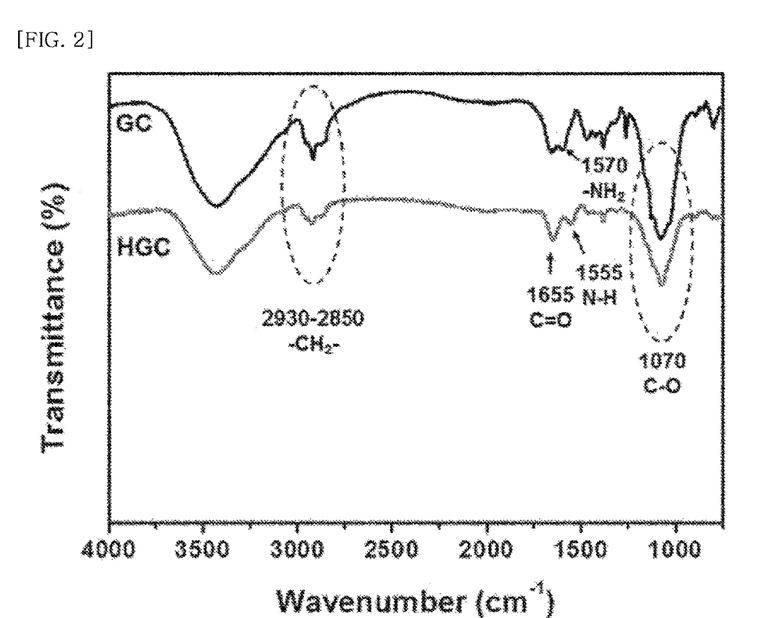
FIG. 2 is an FT-IR spectrum of N-hexanyonylate glycol chitosan according to an embodiment of the present invention.

To investigate whether —NH alkylacyl glycol chitosan prepared as above was synthesized or not, FT-IR analysis was performed. The result is shown in FIG. 2. A specimen was prepared as KBr pellet, and measurement was performed within the range of 750-4000 cm$^{-1}$. For each spectrum of glycol chitosan and N-hexanyonylate glycol chitosan, both wavelength representing stretching vibration of carbonyl bond (C=O) (1655 cm$^{-1}$) and wavelength representing stretching vibration of C-H (2880-2930 cm$^{-1}$) were found. Also, an absorbance wavelength representing bending vibration of primary amine bond appeared at 1596 cm$^{-1}$. For the N-hexanyonylate glycol chitosan spectrum, the peak at 1596 cm$^{-1}$ disappeared, and an absorbance wavelength representing bending vibration of an amide bond (N—H) was found at 1555 cm$^{-1}$.

From these results, it has been found that N-hexanyonylate glycol chitosan was well synthesized.

Sol-Gel Transition Behavior

—NH alkylacyl glycol chitosan prepared above was diluted in PBS to the concentration of 4 wt %, and sol-gel behavior was investigated.

Figure 3:
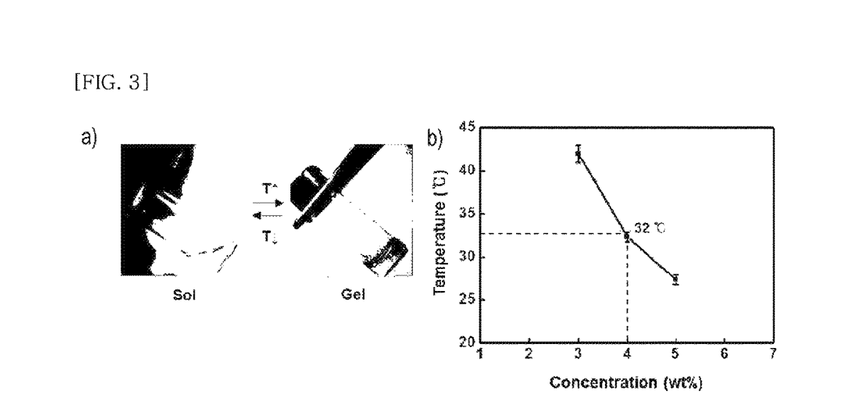

As shown in FIG. 3a), N-hexanyonylate glycol chitosan is in a sol-state, which flows well, at a low temperature, but N-hexanyonylate glycol chitosan becomes a gel-state at a high temperature so that N-hexanyonylate glycol chitosan does not flow well even when the vial is tilted. Consequently, sol-gel phase transition behavior depending on temperature has been confirmed.

The sol-gel transition temperature of N-hexanyonylate glycol chitosan was measured through a tube inverting method, and the result is shown in FIG. 3b). As samples, various concentrations of N-hexanyonylate glycol chitosan diluted in a phosphate-buffer saline (PBS) solution were prepared. The samples were stored at a temperature of 4° C. and dissolved well. The prepared samples were measured by rising temperature by using a Multi-Blok heater. The vial was tilted and observed for 30 seconds. When the sample flowed, the sample was considered as in a sol-state, and the sample did not flow, the sample was considered as in a gel-state.

As shown in FIG. 3b), sol-gel transition was found at 42±1 for N-hexanyonylate glycol chitosan diluted to 3 wt %; 32.3±0.6 for 4 wt %; and 27.3±0.6 for 5 wt %. During the cell culturing experiment, sol-gel transition occurred at a temperature of 37° C. or less in various concentrations so a further experiment was performed by using 4 wt % of N-hexanyonylate glycol chitosan having a lower viscosity.

Preparation Example 2: Preparation of N-Acetylate Glycol Chitosan 0.2 g of glycol chitosan (weight-average molecular weight of 400 kDa, acetylation degree of 9.34±2.50% (measured with $^1$H NMR, Sigma-Aldrich, Inc., USA) was dissolved in 25 ml of distilled water, and then diluted by adding 25 ml of methanol. Precalculated content of acetic acid anhydride (Sigma-Aldrich, Inc., USA) was added to the obtained solution while stirring with a magnetic stirrer.

After continuous stirring at room temperature for 48 hours, precipitation was performed with cold acetone to obtain the reactant, and white solid was obtained through centrifugation. Sequentially, the obtained reactant was treated with 1 mol/L sodium hydroxide solution for 12 hours to remove an O-acetyl group, dialyzed with distilled water for 3 days by using a dialysis membrane having a molecular weight cut-off of 2 kDa, and then freeze dried. The acetylation degree of the obtained N-acetylate glycol chitosan was 92%.

Figure 4:
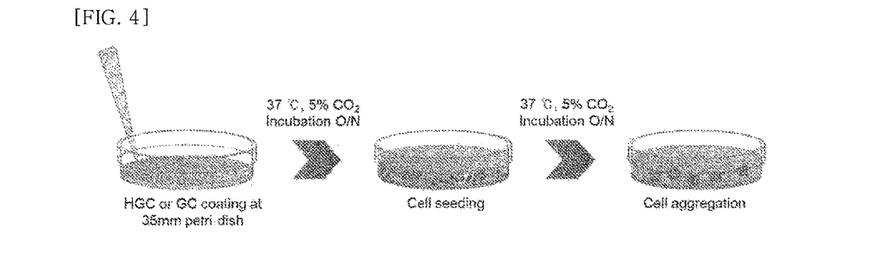
FIG. 4 schematically shows a method for forming a spheroid according to an embodiment of the present invention.

Example 1: Formation of Cell Spheroid by Using Temperature-Sensitive Glycol Chitosan As shown in FIG. 4, 250 ul of glycol chitosan and N-hexanyonylate glycol chitosan, which were dissolved in DMEM medium to 4 wt %, were respectively added to petridishes having a diameter of 35 mm, and speared by using a tip of an injector without a needle such that the glycol chitosan and N-hexanyonylate glycol chitosan were homogeneously spread on the entire bottom. The coated petridishes were stored in 5% $CO_2$ incubator at 37° C. over-night (O/N). After a day, the cultured rat embryonic myocardial cells were treated with trypsin enzyme to be suspended as a single cell. Trypsin was inactivated by using a medium containing serum, and centrifugation was performed to collect cells. A fresh medium was added to the collected cells. Then, the cells were counted. The counted cells were added to the coated 35 mm petridish such that the final medium volume becomes 3 ml. The resultant was cultured in 5% $CO_2$ incubator at 37° C. for about one day. After a day, presence and absence of cell aggregate was investigated through a microscope.

Example 2: Formation of Cell Spheroid by Using Temperature Sensitive Glycol Chitosan 250 ul of matrigel (BD-Matrigel), N-acetylate glycol chitosan, and N-hexanyonylate glycol chitosan, which were dissolved in DMEM medium to 4 wt %, were respectively added to petridishes having a diameter of 35 mm, and speared by using a tip of an injector without a needle such that the Matrigel, N-acetylate glycol chitosan, and N-hexanyonylate glycol chitosan were homogeneously spread on the entire bottom. $6 \times 10^4/100$ ul of vascular progenitor cells derived from cord blood stem cells were seeded on the coated petridishes, and the resultant were stored in 5% $CO_2$ incubator at 37° C. for 24 hours. After a day, presence and absence of cell aggregates was investigated through a microscope. The result was shown in FIG. 5.

Figure 5:
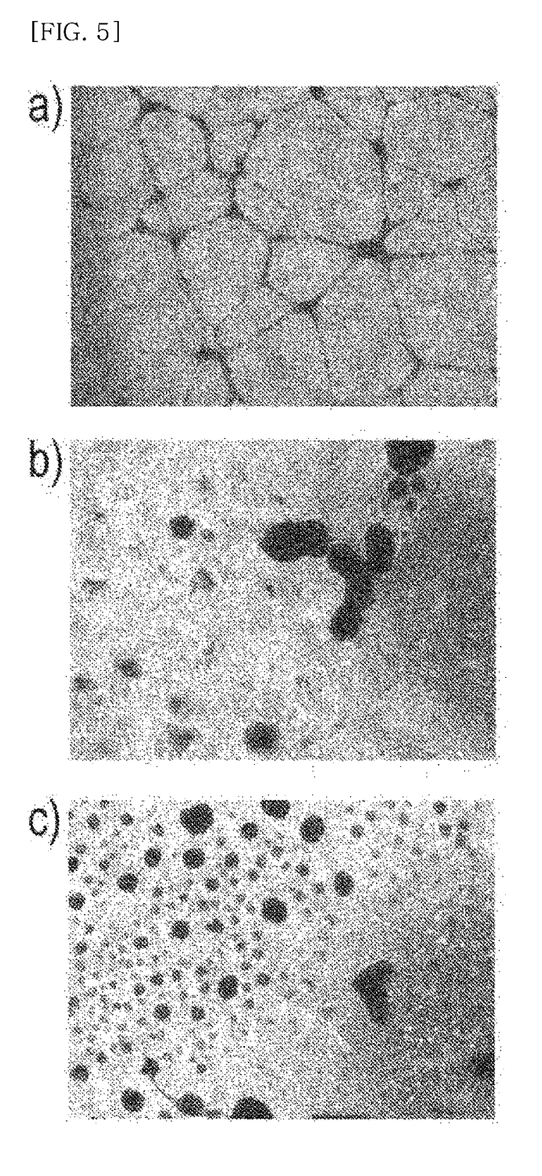
FIG. 5 are images obtained with an optical microscope by observing spheroid formation when vascular endothelial precursor cells are cultured in a matrigel-coated culture container a), an acetylate glycol chitosan-coated culture container b); and an N-hexanyonylate-coated culture container c).

With referring to FIG. 5, it has been found that, unlike the matrigel-coated culture container in which a spheroid was not formed and tubules were formed, cells were aggregated and spheroids were formed in culture containers respectively coated with acetylated glycol chitosan, and N-hexanyonylate glycol chitosan.

Experimental Example 1: Investigation of Cell Growth Rate and Cell Survival Rate A 96-well plate was coated with collagen. $2 \times 10^4/100$ ul myocardial cells isolated from rat embryo were seeded. On the next day, replacement with glycol chitosan, and N-hexanyonylate glycol chitosan media diluted to 1 wt % was performed. The day after seeding the cells was considered as day 1. Replacement with a fresh medium was performed at an interval of 1, 3, 5, and 7 days. MTT analysis was daily performed to investigate the cell growth rate depending on days.

20 ul of 5 mg/ml MTT reagent was dispensed to each well, and the resultant was incubated for 2 hours in a 5% $CO_2$ incubator at 37° C. Total medium in the well was removed, and 150 ul of DMSO was dispensed. The plate was sealed with a foil to block light, and left at room temperature for 15 minutes. An absorbance was measured at 540 nm by using Spectra Max. The result is shown in FIG. 5A.

A cover slip having a diameter of 12 mm was coated with collagen, and added to a 24-well plate. $1 \times 10^5$ of myocardial cells isolated from a rat embryo were seeded. On the next day, replacement with glycol chitosan, and N-hexanyonylate glycol chitosan media diluted to 1 wt % were performed. After days of medium replacement, live-dead assay (abcam, ab65470) was performed. The result is shown in FIG. 6B.

Figure 6:
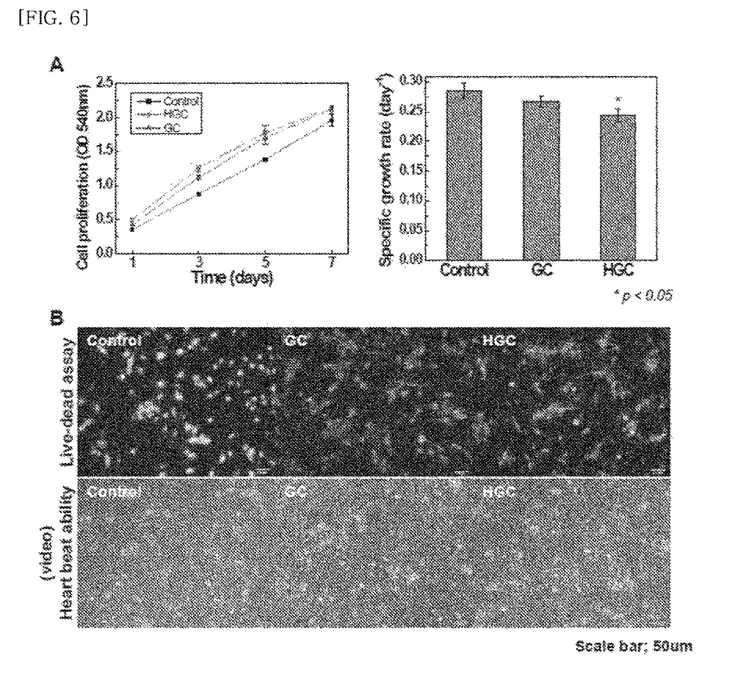
FIG. 6A is a graph comparing cell growth rates and cell viabilities when myocardial cells are cultured in a normal container, glycol chitosan-coated container, or N-hexanyonylate glycol chitosan-coated container.
FIG. 6B is an image showing live/dead assay result when myocardial cells are cultured in a normal culture container, glycol chitosan-coated container, or N-hexanyonylate glycol chitosan-coated container.

As shown in FIG. 6B, green fluorescence represents live cells and red fluorescence represents dead cells. Although some cells represented red fluorescence in glycol chitosan and N-hexanyonylate glycol chitosan, high survival rates were shown. Consequently, it has been found that glycol chitosan and N-hexanyonylate glycol chitosan less affect cell survival rates.

Experimental Example 2: Investigation of Myocardial Cell Spheroid Formation Depending on Number of Cells and Survival Rate of Cell Spheroid During Long Term Culture To investigate an influence of glycol chitosan and N-hexanyonylate glycol chitosan on 3-dimensional spheroid formation of myocardial cells, various concentrations of myocardial cells were respectively cultured on a petridish, glycol chitosan coated dish, and N-hexanyonylate glycol chitosan coated dish.

$0.5 \times 10^5$, $1 \times 10^5$, $2 \times 10^5$, $5 \times 10^5$, and $10 \times 10^5$ myocardial cells were diluted in 3 mL of DMEM medium in which 10% serum and 1× penicillin/streptomycin were added. The cells were respectively dispensed to the prepared 35 mm petridish, glycol chitosan-coated petridish and N-hexanyonylate glycol chitosan-coated petridish. The resultant was incubated a day in a 5% $CO_2$ incubator at 37° C. Spheroid formation in each petridish depending on the cell concentration and time were observed through an optical microscope at ×100 magnification. The results are shown in FIGS. 6A and B.

Figure 7:
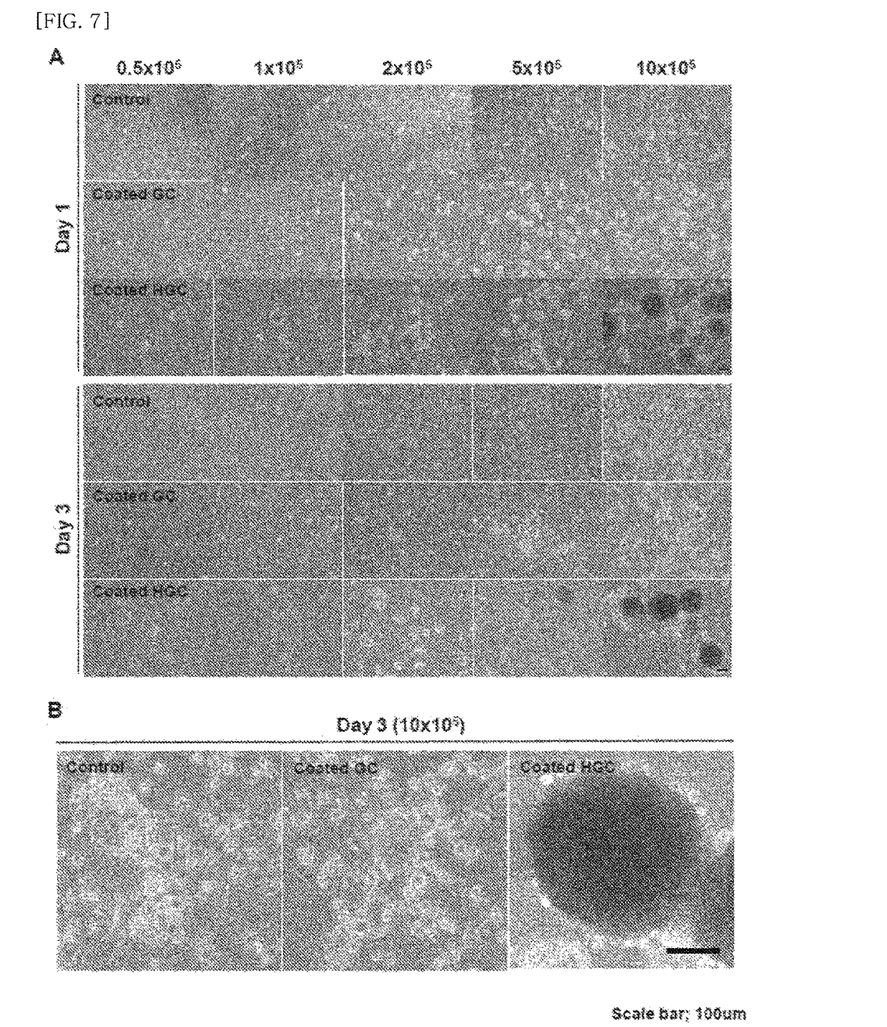
FIG. 7 is an image obtained by observing spheroid formation depending on the number of cells with an optical microscope when myocardial cells are cultured in a normal culture container, glycol chitosan-coated container, or N-hexanyonylate glycol chitosan-coated container.

As shown in FIGS. 7A and B, for dishes respectively coated with glycol chitosan and N-hexanyonylate glycol chitosan, spheroids were formed on day 1. The Spheroid was well formed in $2 \times 10^5$-$10 \times 10^5$ myocardial cells. For the control petridish, as the number of cells increased, some of cells formed spheroid, while remaining was left as a single cell and suspended. In addition, several single cells were adhered to the bottom of the dish. It should be noted that, although the number was small, for the dish coated with N-hexanyonylate glycol chitosan, the spheroid had the similar size as that of the spheroid formed in the glycol chitosan coating group of $2 \times 10^5$ cells.

It has been found that most of myocardial cells in the control petridish were maintained in a single cell state and adhered to the bottom. For the myocardial cells cultured in the petridish coated with glycol chitosan, it has been found that the formed spheroid was adhered to the bottom, and single cells around the spheroid were also adhered to the bottom. On the contrary, for N-hexanyonylate glycol chitosan, it has been found that spheroid was not adhered to the bottom and well maintained. After 3 days, most of cells in the petridish group were adhered to the bottom, and small number of formed spheroids was also adhered. It has been found that, in the glycol chitosan-coated dishes, the spheroid formed on day 1 was adhered to the bottom and cells were spread to the surrounding area. For the N-hexanyonylate glycol chitosan coated dish, it has been found that the similar state as day 1 was maintained, and spheroid was not adhered to the bottom and maintained well in a suspended state.

Consequently, in terms of forming a spheroid, the dish coated with N-hexanyonylate glycol chitosan was easily used for long term experiment because the spheroid was formed with a small number of cells without particular difficulty and the formed spheroid was still maintained for 3 days.

Figure 8:
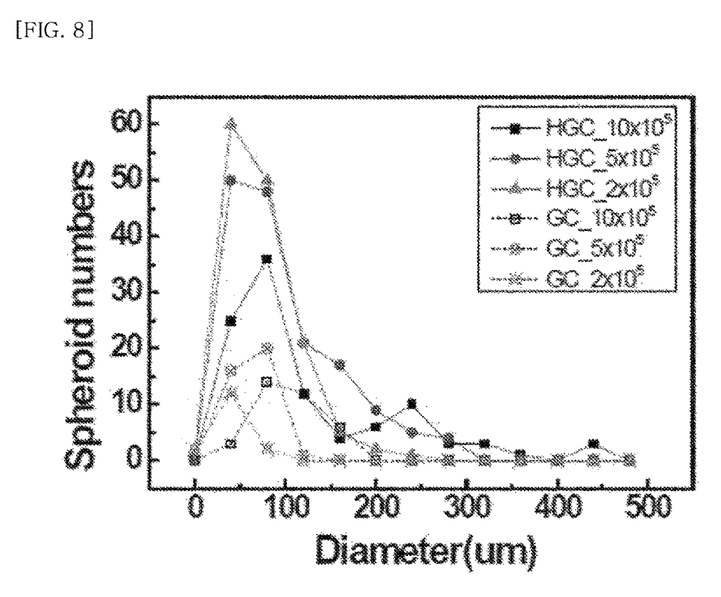
FIG. 8 is a graph showing distribution of myocardial spheroid diameters depending on cell concentrations when myocardial cells are cultured in a glycol chitosan-coated container, or N-hexanyonylate glycol chitosan-coated container.

FIG. 8 is a graph showing diameter distribution of the myocardial cell spheroid depending on cell concentration when the myocardial cells were respectively cultured in the glycol chitosan-coated dish and the N-hexanyonylate glycol chitosan-coated dish.

To investigate the degree of spheroid formation and diameter distribution of the spheroid for various cell concentrations, the formed spheroid was cultured for 3 days. Then, the diameter was measured and the number of spheroid was counted.

With referring to FIG. 8, when glycol chitosan-coated dish and N-hexanyonylate glycol chitosan-coated dish, in which $2 \times 10^5$ cells were cultured, were compared, it has been found that most of the spheroids have a diameter of about 40 um for the glycol chitosan-coated dish and most of the spheroids have a diameter of about 100 um or less for the N-hexanyonylate glycol chitosan-coated dish, and also the number of spheroid of the N-hexanyonylate glycol chitosan-coated dish was higher than that of the glycol chitosan. When the coated dishes in which $5 \times 10^5$ cells were cultured were compared, it has been found that the myocardial cell spheroids cultured in the glycol chitosan-coated dish have a diameter distribution of 100 um or less, while most of the spheroids cultured in the N-hexanyonylate glycol chitosan-coated dish have a diameter distribution of 150 um or less, and the larger number of spheroid was formed in the N-hexanyonylate glycol chitosan-coated dish than that of the glycol chitosan. For $10 \times 10^5$, most of the spheroids in the both glycol chitosan-coated dish and N-hexanyonylate glycol chitosan-coated dish had a diameter of 150 um or less. However, it has been found that, for the N-hexanyonylate glycol chitosan-coated dish, the larger number of spheroid was formed, and a spheroid having a diameter of around 250 um was also formed.

The prepared spheroids were cultured for 3 and 7 days, and live-dead assay was performed at a spheroid state. Images were captured with a confocal fluorescent microscope. The result is shown in FIG. 9.

Figure 9:
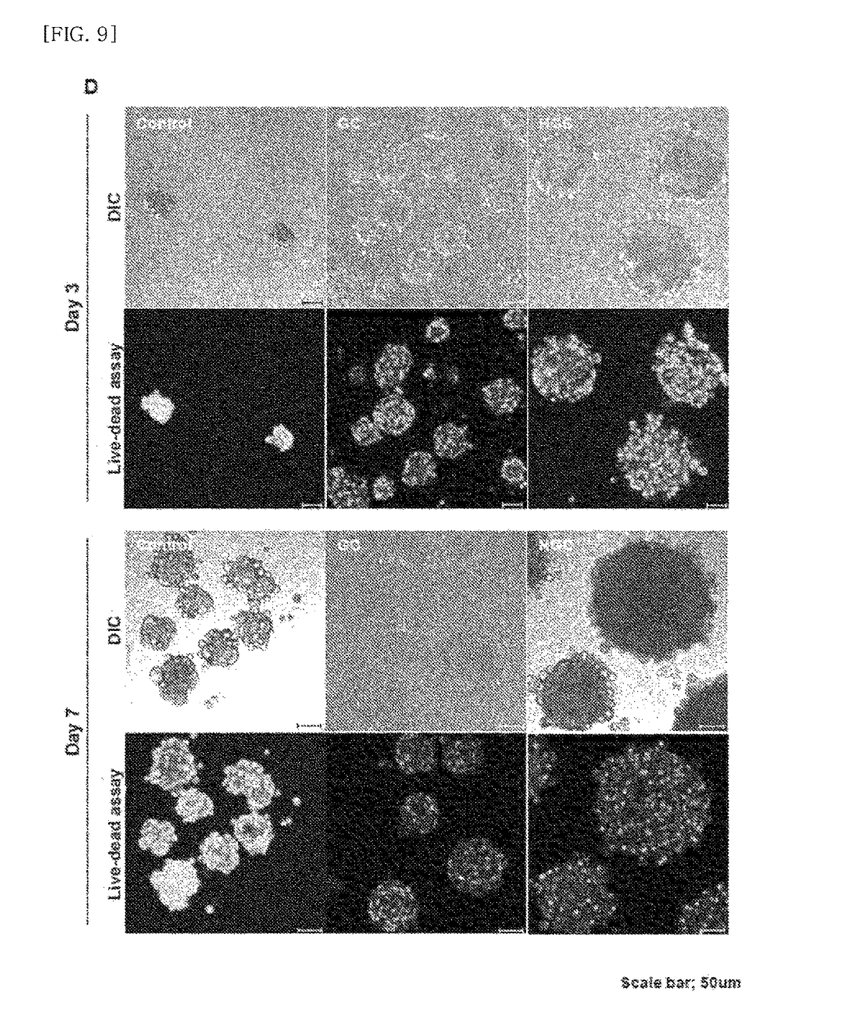
FIG. 9 is a confocal fluorescence microscopic image showing the result of respectively culturing the formed myocardial cell spheroid in a normal culture container, glycol chitosan-coated container, or N-hexanyonylate glycol chitosan-coated container for 3 and 7 days and then analyzing live/dead of the spheroid.

As shown in FIG. 9, most of the petridish and N-hexanyonylate glycol chitosan-coated dish showed green fluorescence, and dead cells were hardly observed. On the contrary, for the spheroid in the glycol chitosan-coated dish on day 3, it has been found that dead cells were distributed from the inside of the spheroid. For day 7, the result similar to the result of day 3 was obtained. It has been found that, although more dead cells were observed in the spheroid of the N-hexanyonylate glycol chitosan-coated dish on day 7, the survival rate was higher than that of glycol chitosan when comparison was performed based on the size of the spheroid.

Further, the myocardial cell spheroids were maintained for 10 days in the glycol chitosan and N-hexanyonylate glycol chitosan coated dishes. When glycol chitosan coating was compared with the N-hexanyonylate glycol chitosan coating, heartbeat intensity for N-hexanyonylate glycol chitosan was more continuous and persistent than heartbeat intensity for glycol chitosan.

Figure 10:
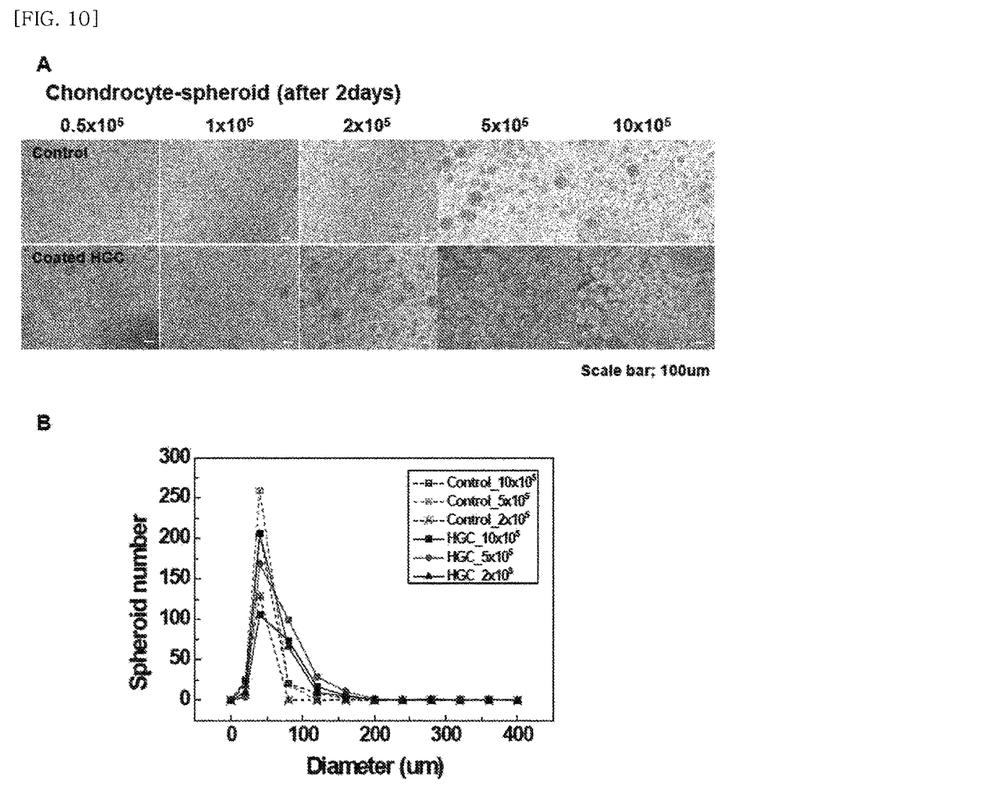
FIG. 10 is an image obtained by observing spheroid formation depending on the number of cells with an optical microscope when condrocytes are cultured in a normal culture container, or N-hexanyonylate glycol chitosan-coated container.

Experimental Example 3: Diameter Distribution of Condrocyte Spheroid Depending on Cell Concentration The same experiment was performed by using other types of cells to investigate whether the result similar to that of myocardial cells was obtained. Condrocytes were used. Various numbers of cells were dispensed on the N-hexanyonylate glycol chitosan-coated dish, and observed after 2 days. The result is shown in FIG. 9. As shown in FIG. 10, unlike the myocardial cells, it has been observed that a condrocyte spheroid was well formed in the control petridish, and a spheroid was formed well even with the small number of cell for the case of N-hexanyonylate glycol chitosan.

Experimental Example 4: Comparison with Hanging Drop Method for Time Required for Spheroid Formation Among the typical methods for preparing a spheroid, the hanging drop method, which uses gravity, is to drop a medium including cells to a cover of a petridish dropwise to cover. The method is advantageous to prepare a spheroid having a homogenous size. However, as the number of prepared spheroid increases, much time is consumed and it is difficult to handle. The time required for preparing 1000 spheroids was compared with that of the N-hexanyonylate glycol chitosan-coated dish and shown in FIG. 11.

Figure 11:
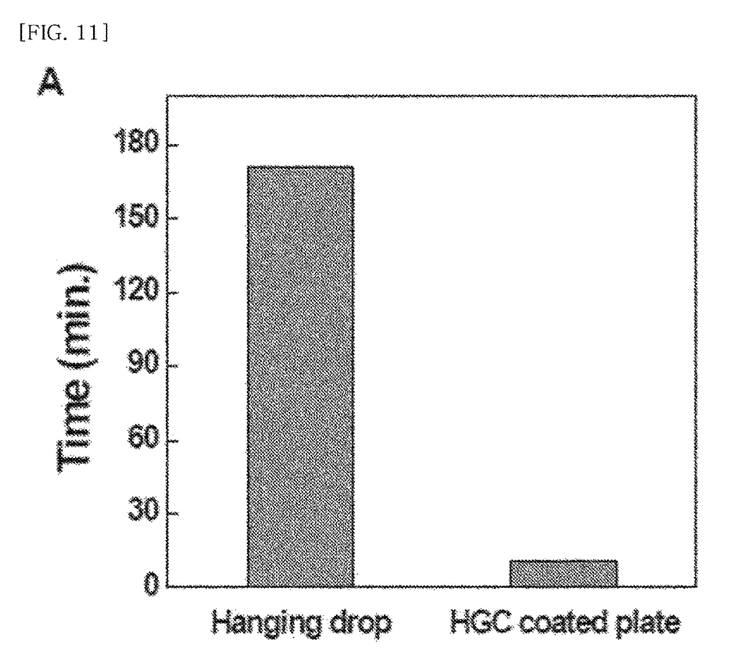
FIG. 11 is a graph comparing time required for spheroid formation for the hanging-drop method and a method for forming a spheroid using an N-hexanyonylate glycol chitosan-coated container.

With referring to FIG. 11, when the N-hexanyonylate glycol chitosan-coated dish was used, the time required for spheroid formation was significantly shortened compared to that of the typical hanging drop method.

The invention claimed is:

1. A spheroid forming method comprising:
    using a culture container in which a surface of a culturing space is coated with a glycol chitosan derivative of the following Chemical Formula 1:

[Chemical Formula 1]

wherein,
$R_1$ is a C1-C18 alkyl group;
X, y, and z are an integer from 10 to 10000; and mol % thereof is $0.05 \leq x \leq 0.8$, $0.05 \leq y \leq 0.15$, and $0.05 \leq z \leq 0.9$;
placing cells for culturing in the culture container; and culturing the cells in the culture container to form spheroids.

2. The method of claim 1, wherein the glycol chitosan derivative of Chemical Formula 1 has a substitution degree of 20-95%.

3. The method of claim 1, wherein the glycol chitosan derivative comprises one compound selected from the following compounds:
    N-propionylate glycol chitosan;
    N-butyroylate glycol chitosan;
    N-pentanyonylate glycol chitosan;
    N-hexanyonylate glycol chitosan; and
    N-acetylate glycol chitosan.

4. The method of claim 1, wherein the glycol chitosan derivative has a weight average molecular weight of 200-5,000,000.

5. The method of claim 1, wherein the glycol chitosan derivative forms hydrogel formed at a temperature the same as or higher than a phase transition critical temperature without formation of a chemical cross-linking.

6. The method of claim 5, wherein the phase transition critical temperature is 37° C. or less.

7. The method of claim 5, wherein a formed spheroid is separated by reducing a temperature of the glycol chitosan derivative to less than the phase transition critical temperature.

* * * * *